(12) United States Patent
Chakkingal et al.

(10) Patent No.: US 12,378,172 B2
(45) Date of Patent: Aug. 5, 2025

(54) PROCESS FOR RECOVERING CRACKED PRODUCT

(71) Applicant: UOP LLC, Des Plaines, IL (US)

(72) Inventors: Susmitha Chakkingal, Gurgaon (IN); Minaz Makhania, Gurgaon (IN); Matthew R. Wojtowicz, Carpentersville, IL (US)

(73) Assignee: UOP LLC, Rosemont, IL (US)

( * ) Notice: Subject to any disclaimer, the term of this patent is extended or adjusted under 35 U.S.C. 154(b) by 119 days.

(21) Appl. No.: 18/503,050

(22) Filed: Nov. 6, 2023

(65) Prior Publication Data

US 2024/0158323 A1    May 16, 2024

(30) Foreign Application Priority Data

Nov. 16, 2022  (IN) .............................. 202211065725

(51) Int. Cl.
*C07C 7/11*  (2006.01)
*C07C 4/06*  (2006.01)
*C10G 55/06*  (2006.01)

(52) U.S. Cl.
CPC .................. *C07C 7/11* (2013.01); *C07C 4/06* (2013.01); *C10G 55/06* (2013.01)

(58) Field of Classification Search
CPC .. C07C 7/11; C07C 4/06; C10G 55/06; C10G 70/06
See application file for complete search history.

(56) References Cited

U.S. PATENT DOCUMENTS

| 1,924,196 | A | * | 8/1933 | Miller ...................... C10G 7/02 |
| | | | | 208/356 |
| 5,372,704 | A | * | 12/1994 | Harandi ................. C10G 11/18 |
| | | | | 208/77 |
| 2018/0273853 | A1 | | 9/2018 | Qafisheh et al. |

* cited by examiner

*Primary Examiner* — Thuan D Dang
(74) *Attorney, Agent, or Firm* — Paschall & Associates, LLC; James C. Paschall

(57) ABSTRACT

A process for catalytic cracking recovery locates the stripping column to receive the main column receiver liquid. The columns purposed for removing light hydrocarbons from the liquid streams are removed from the high-pressure section thus saving energy.

18 Claims, 1 Drawing Sheet

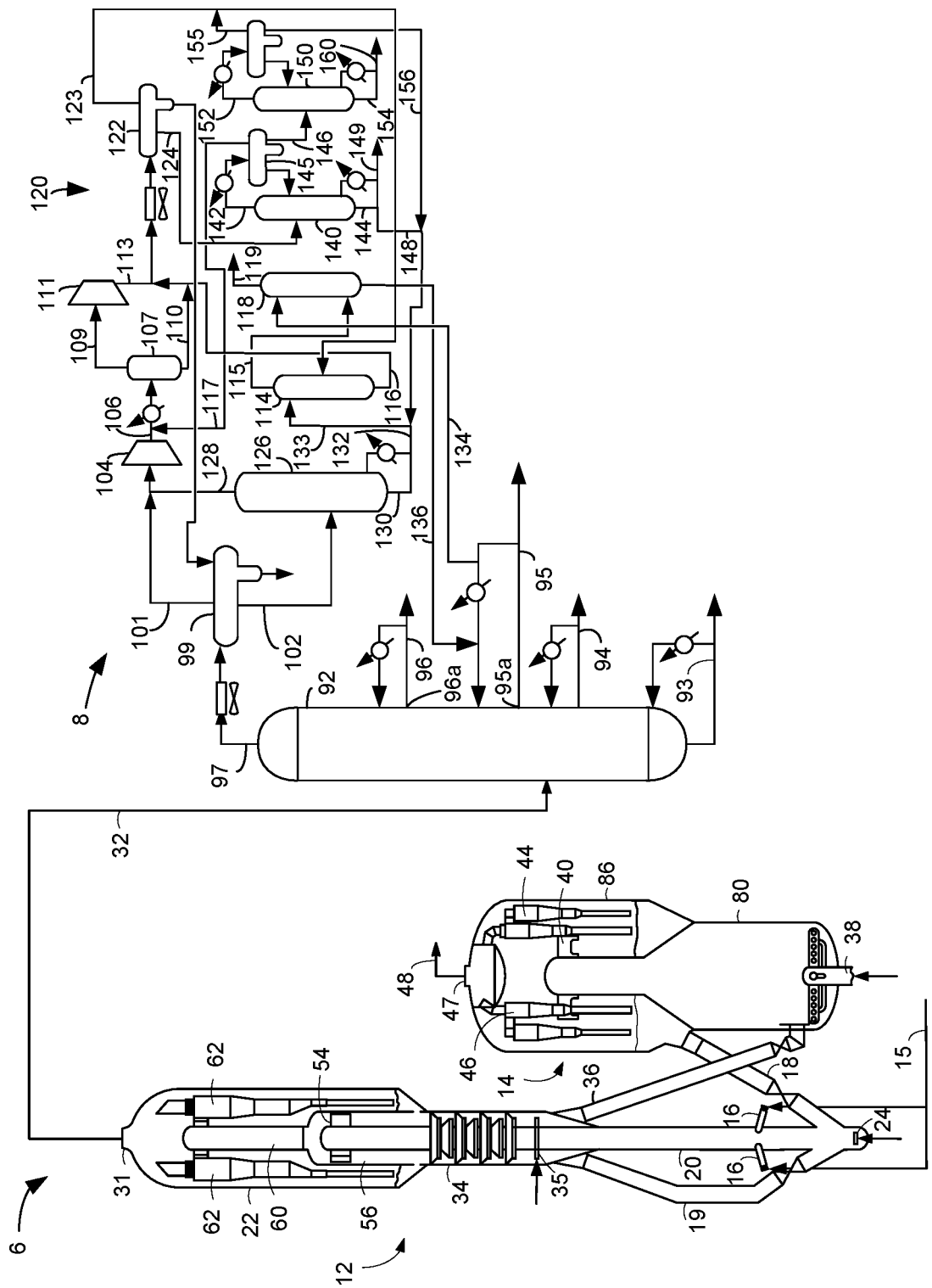

PROCESS FOR RECOVERING CRACKED PRODUCT

FIELD

The field is the recovery of cracked product from the reaction of feed with fluid catalyst. The field particularly relates to a fluid catalytic process to recover cracked product with abundant light olefins.

BACKGROUND

Catalytic cracking can create a variety of products from larger hydrocarbons. Often, a feed of heavier hydrocarbons, such as a vacuum gas oil, is provided to a catalytic cracking reactor, such as a fluid catalytic cracking (FCC) reactor. Various products may be produced, including a gasoline product and/or light product such as propylene and/or ethylene. Spent catalyst is regenerated by combustion and returned to the catalytic cracking reactor.

FCC effluent is directed to a main column for cooling and fractionation of products. A gas concentration section in the FCC unit is responsible for recovering lighter hydrocarbons from the main column overhead. FCC units are being designed to produce more propylene to meet the demands of the plastics industry. Greater propylene production pushes capacity of the gas concentration section. The gas concentration section often includes a large recycle loop from a debutanizer bottoms to a primary absorber column in a high-pressure section. The stripper column in this loop requires much energy to boil up the light gases in the high-pressure section that are recycled to the primary absorber column.

Thus, there is a desire to provide a recovery system for catalytic cracking that can reduce energy required for recovering greater quantities of ethylene and propylene product.

BRIEF SUMMARY

A process for catalytic cracking locates the stripping column to receive the main column overhead receiver liquid. The columns purposed for removing light hydrocarbons from the liquid streams are removed from the high-pressure section thus reducing heating duty.

Additional details and embodiments of the invention will become apparent from the following detailed description of the invention.

BRIEF DESCRIPTION OF THE DRAWING

The FIGURE is a schematic, elevational view of the process of the present disclosure.

Definitions

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, the term "predominant" or "predominate" means greater than 50%, suitably greater than 75% and preferably greater than 90%.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure. A receiver is a type of separator.

As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures".

As used herein, the term "True Boiling Point" (TBP) means a test method for determining the boiling point of a material which corresponds to ASTM D-2892 for the production of a liquefied gas, distillate fractions, and residuum of standardized quality on which analytical data can be obtained, and the determination of yields of the above fractions by both mass and volume from which a graph of temperature versus mass % distilled is produced using fifteen theoretical plates in a column with a 5:1 reflux ratio.

As used herein, the term "T5" or "T95" means the temperature at which 5 mass percent or 95 mass percent, as the case may be, respectively, of the sample boils using ASTM D-86 or TBP.

As used herein, the term "initial boiling point" (IBP) means the temperature at which the sample begins to boil using ASTM D-7169, ASTM D-86 or TBP, as the case may be.

As used herein, the term "end point" (EP) means the temperature at which the sample has all boiled off using ASTM D-7169, ASTM D-86 or TBP, as the case may be.

As used herein, "vacuum gas oil" means a hydrocarbon material having an IBP of at least about 232° C. (450° F.), a T5 of between about 288° C. (550° F.) and about 392° C. (700° F.), typically no more than about 343° C. (650° F.), a T95 between about 510° C. (950° F.) and about 570° C. (1058° F.) and, or an EP of no more than about 626° C.

(1158° F.) prepared by vacuum fractionation of atmospheric residue as determined by any standard gas chromatographic simulated distillation method such as ASTM D2887, D6352 or D7169, all of which are used by the petroleum industry.

As used herein, "atmospheric residue" means a hydrocarbon material having an IBP of at least about 232° C. (450° F.), a T5 of between about 288° C. (550° F.) and about 392° C. (700° F.), typically no more than about 343° C. (650° F.), and a T95 between about 510° C. (950° F.) and about 700° C. (1292° F.) obtained from the bottoms of an atmospheric crude distillation column.

As used herein, "vacuum residuum" means hydrocarbon material boiling with an IBP of at least about 500° C. (932° F.).

DETAILED DESCRIPTION

The FCC gas concentration section often includes a large recycle loop from a debutanizer column bottoms to a primary absorber column. The proposed process intends to remove this recycle stream from the high-pressure section by rearranging the stripper column to immediately downstream of a main column overhead receiver. Operation of the stripper column is thus enabled at lower pressure, reducing the energy consumption in a stripper reboiler. C5+ hydrocarbons from a stripper column bottoms will be routed to the primary absorber column as the absorbent. Removing lights from the absorbent to the primary absorber column improve the absorption.

Now turning to the FIGURE, wherein like numerals designate like components, a process generally includes an FCC unit section 6 and a product recovery section 8. The FCC unit section 6 includes a FCC reactor 12 and a catalyst regenerator 14. Process conditions in the FCC reactor 12 may include a cracking reaction temperature of about 400° to about 600° C., preferably about 538° C. to about 593° C. at the reactor outlet, and a catalyst regeneration temperature of about 500° to about 900° C. Both the cracking and regeneration occur at an absolute pressure between about 100 kPa (14 psia) to about 650 kPa (94 psia), preferably between about 140 kPa (20 psia) to about 450 kPa (65 psia).

FIG. 1 shows the FCC reactor 12 in which a hydrocarbon feedstock in line 15 distributed through a distributor 16 is contacted with a stream of fluid catalyst entering from a regenerated catalyst standpipe 18 and a recirculation catalyst standpipe 19. The hydrocarbon feedstock may comprise vacuum gas oil, atmospheric resid, deasphalted oil, vacuum resid or any other stream processed in a conventional FCC unit.

The catalyst can be a single catalyst or a mixture of different catalysts. Usually, the catalyst includes two components or catalysts, namely a first component or catalyst, and a second component or catalyst. Such a catalyst mixture is disclosed in, e.g., U.S. Pat. No. 7,312,370 B2. Generally, the first component may include any of the well-known catalysts that are used in the art of FCC, such as an active amorphous clay-type catalyst and/or a high activity, crystalline molecular sieve. Zeolites may be used as molecular sieves in FCC processes. Preferably, the first component includes a large pore zeolite, such as a Y-type zeolite, an active alumina material, a binder material, including either silica or alumina, and an inert filler such as kaolin.

Typically, the zeolitic molecular sieves appropriate for the first component have a large average pore size. Usually, molecular sieves with a large pore size have pores with openings of greater than about 0.7 nm in effective diameter defined by greater than about 10, and typically about 12, member rings. Pore Size Indices of large pores can be above about 31. Suitable large pore zeolite components may include synthetic zeolites such as X and Y zeolites, mordenite and faujasite. A portion of the first component, such as the zeolite, can have any suitable amount of a rare earth metal or rare earth metal oxide.

The second component may include a medium or smaller pore zeolite catalyst, such as a MFI zeolite, as exemplified by at least one of ZSM-5, ZSM-11, ZSM-12, ZSM-23, ZSM-35, ZSM-38, ZSM-48, and other similar materials. Other suitable medium or smaller pore zeolites include ferrierite, and erionite. Preferably, the second component is a medium or small pore zeolite dispersed on a matrix including a binder material such as silica or alumina and an inert filler material such as kaolin. The second component may also include some other active material such as Beta zeolite. These compositions may have a crystalline zeolite content of about 10 to about 50 wt % or more, and a matrix material content of about 50 to about 90 wt %. Components containing about 40 wt % crystalline zeolite material are preferred, and those with greater crystalline zeolite content may be used. Generally, medium and smaller pore zeolites are characterized by having an effective pore opening diameter of less than or equal to about 0.7 nm, rings of about 10 or fewer members, and a Pore Size Index of less than about 31.

The total catalyst mixture in the FCC reactor 12 may contain about 1 to about 25 wt % of the second component, namely a medium to small pore crystalline zeolite with greater than or equal to about 1.75 wt % of the second component being preferred. The first component may comprise the balance of the catalyst composition. In some preferred embodiments, the relative proportions of the first and second components in the mixture may not substantially vary throughout the FCC reactor 12. The high concentration of the medium or small pore zeolite as the second component of the catalyst mixture can improve selectivity to light olefins. In one exemplary embodiment, the second component can be a ZSM-5 zeolite and the mixture can include about 4 to about 10 wt % ZSM-5 zeolite excluding any other components, such as binder and/or filler.

Preferably, at least one of the first and/or second catalysts is an MFI zeolite having a silicon to aluminum ratio greater than about 15, preferably greater than about 75. In one exemplary embodiment, the silicon to aluminum ratio can be about 15:1 to about 35:1.

The contacting may occur in a narrow riser 20, extending upwardly to the bottom of a reactor vessel 22. The contacting of the hydrocarbon feedstock and the first stream of fluid catalyst is fluidized by gas such as steam from a fluidizing distributor 24. In an embodiment, heat from the catalyst vaporizes the hydrocarbon feedstock, and the hydrocarbon feedstock is thereafter cracked to a cracked product stream of lighter molecular weight in the presence of the first catalyst stream as both are transferred up the riser 20 into the reactor vessel 22 providing a mixture of catalyst and product gases.

The pressure in the riser 20 may be about 200 kPa (29 psia) to about 450 kPa (65 psia), but it could be lower. A steam rate of about 3 to about 7 wt % of the hydrocarbon feedstock is added to the riser 20. Inevitable side reactions occur in the riser 20 leaving coke deposits on the catalyst that lower catalyst activity to provide a spent catalyst stream. The cracked product stream in the mixture of catalyst and product gases is thereafter separated from the spent catalyst stream using cyclonic separators which may include one or two stages of cyclones 62 in the reactor vessel 22. A gaseous, cracked product stream exits the reactor vessel 22 through a product outlet 31 to line 32 for transport to the downstream product recovery section 8.

The spent or coked catalyst requires regeneration for further use. The spent catalyst stream, after separation from the cracked product stream by means of a disengagement device 54 in a disengagement chamber 56, falls into a stripping section 34 where steam is injected through a distributor 35 to purge any residual hydrocarbon vapor. After the stripping operation, the stripped coked catalyst is carried to the catalyst regenerator 14 through a spent catalyst standpipe 36. Another portion of the stripped coked catalyst may be recycled to the riser 20 by the recirculation catalyst standpipe 19 without undergoing regeneration.

FIG. 1 depicts a regenerator 14 known as a combustor. However, other types of regenerators are suitable. In the catalyst regenerator 14, a stream of oxygen-containing gas, such as air, is introduced through an air distributor 38 to contact the coked catalyst. Coke is combusted from the coked catalyst in a combustion chamber 80 to provide regenerated catalyst and flue gas. The catalyst regeneration process adds a substantial amount of heat to the catalyst, providing energy to offset the endothermic cracking reactions occurring in the riser 20. Catalyst and air flow upwardly together in the combustion chamber 80 of regenerator 14 and, after regeneration, are initially separated by discharge through a disengager 40 and enter a separation chamber 86. Additional recovery of the regenerated catalyst and flue gas exiting the disengager 40 is achieved using first and second stage separator cyclones 44, 46, respectively within the separation chamber 86 of the catalyst regenerator 14. Catalyst separated from flue gas dispenses through diplegs from cyclones 44, 46 while flue gas relatively lighter in catalyst sequentially exits cyclones 44, 46 and exits the regenerator vessel 14 through flue gas outlet 47 in a flue gas line 48. Regenerated catalyst is carried back to the riser 20 through the regenerated catalyst standpipe 18. As a result of the coke burning, the flue gas vapors exiting at the top of the catalyst regenerator 14 contain $CO$, $CO_2$, $N_2$ and $H_2O$, along with smaller amounts of other species.

The product recovery section 8 is in downstream communication with the product outlet 31. In the product recovery section 8, the cracked product stream in line 32 is directed to a lower section of an FCC main fractionation column 92. The main column 92 is in downstream communication with the product outlet 31. Several fractions of FCC product may be separated and taken from the main column including a heavy slurry oil from the bottoms in line 93, a heavy cycle oil stream in line 94, a light cycle oil in line 95 taken from outlet 95*a* and a heavy naphtha stream in line 96 taken from outlet 96*a*. Any or all of lines 93-96 may be cooled and pumped back to the main column 92 to cool the main column typically at a higher location. Gasoline and gaseous light hydrocarbons are removed in a main overhead line 97 from the main column 92 and condensed before entering a main column receiver 99. The main column receiver 99 is in downstream communication with the product outlet 31, and the main column 92 is in upstream communication with the main column receiver 99.

An aqueous stream is removed from a boot in the main column receiver 99. Moreover, a main net gas stream is removed in a receiver overhead line 101 while a condensed main overhead net liquid stream comprising light naphtha is removed in the receiver bottoms line 102. The main net gas stream in line 101 contains gaseous light hydrocarbons which are very olefinic. The main net gas stream in line 101 may enter a vapor recovery section 120 of the product recovery section 8.

The condensed, main net liquid stream comprising unstabilized, light naphtha stream in the receiver bottoms line 102 is transported to a stripper column 126. Preferably the main net liquid stream in the receiver bottoms line 102 is sent directly to the stripper column 126. Hence, the stripper column 126 is in direct, downstream communication with the main column receiver 99 through the receiver bottoms line 102. Most of the C2− hydrocarbons and light gases are removed in a stripper overhead stream in a stripper overhead line 128 extending from an overhead of the stripper column 126 and transported to a first stage compressor 104 in upstream communication with the first stage compressor 104 along with the main net gas stream in the receiver overhead line 101. The stripper overhead stream in line 128 contains small amounts of C3-C5 hydrocarbons. A stripped bottom stream in a stripper bottoms line 130 extending from a bottom of the stripper column 126 comprising C3+ hydrocarbons from a bottom of the stripper 126 is split into a reboil stream which is boiled up and returned to the column and a net stripped stream in a net stripper bottoms line 132. The stripper column 126 may operate a bottoms temperature of about 140° C. to about 175° C. and an overhead pressure of about 200 kPa to about 400 kPa. The stripper column 126 is not located on the high-pressure lines and is operated at a lower pressure, reducing energy consumption in the stripper reboiler.

The vapor recovery section 120 is shown to be an absorption-based system, but any vapor recovery system may be used including a cold box system. To obtain sufficient separation of light gas components, the main net gas stream in line 101 and a stripper overhead stream in line 128 are compressed in a first stage compressor 104. At least one compressor stage may be used, and typically a dual stage compression is utilized. The first compressed main net gas stream in line 106 is joined by a vapor light hydrocarbon stream in a net fractionation overhead line 117, cooled and fed to an interstage separator 107. The interstage separator 107 separates the first compressed main net gas stream and the vapor light hydrocarbon stream into a first stage main net vapor stream in line 109 and a first stage main liquid stream in line 110. The first stage main net gas stream in line 109 is compressed in a second stage compressor 111 to provide a second compressed main net gas stream in line 113. The second compressed main net gas stream is joined by a rich absorbent stream in a primary absorber bottoms line 116 and the first stage liquid stream in line 110, chilled and delivered to a high-pressure receiver 122. The high-pressure receiver 122 separates the chilled second compressed main net gas stream, the rich absorbent stream and the first stage liquid stream into a gaseous hydrocarbon stream in a high-pressure receiver overhead line 123 comprising C2− hydrocarbons and a liquid hydrocarbon stream in a high-pressure receiver bottoms line 124 comprising C3+ hydrocarbons. An aqueous stream from the high-pressure receiver 122 may be routed to the main column receiver 99.

The gaseous hydrocarbon stream in line 123 is routed to a primary absorber column 114 in which it is contacted with a primary absorbent in a primary absorbent line 133 to effect a separation between C2− and C3+ hydrocarbons. The primary absorbent includes the net stripped bottom stream in line 132 from the bottom of the stripper column 126, net heavy hydrocarbon stream in a fractionation bottoms line 148, and a deethanizer overhead liquid stream in a deethanizer receiver bottoms line 156. The primary absorber 114 is in downstream communication with the stripping column 126 and the main column receiver 99. The primary absorber column 114 may be in direct downstream communication with the bottom of the stripping column 126 through the stripper bottoms line 130. In the primary absorber column 114 the net stripped bottom stream in line 132, perhaps via the primary absorbent line 133, is contacted with the gaseous hydrocarbon stream in line 123 to absorb C3+ hydrocarbons from a gaseous hydrocarbons stream to provide an absorbed gaseous hydrocarbon stream in an absorber overhead line 115 and the rich absorbent stream in the primary absorber bottoms line 116. The net stripped bottom stream in line 132 perhaps in the primary absorbent line 133 is fed to the primary absorber column 114 at a higher elevation and the gaseous hydrocarbon stream in line 123 is fed at a lower elevation to the column to effect counter current contact in the primary absorber 114. The primary absorber 114 is able to remove C3 and C4 hydrocarbons by contact with the net stripper bottoms stream as the primary absorbent. As mentioned, the net heavy hydrocarbon stream in the fractionation bottoms line 148 from a fractionation column 140 and the deethanizer overhead liquid stream in the deethanizer receiver bottoms line 156 may supplement the net stripped bottom stream to provide sufficient primary absorbent in the primary absorbent line 133. Hence, the gaseous hydrocarbon stream in line 123 may also be contacted with the net heavy hydrocarbon stream in line 148 and/or the deethanizer overhead liquid stream in line 156 to absorb C3+ hydrocarbons from the gaseous hydrocarbon stream.

The C3+ hydrocarbon rich absorbent stream in line 116 is returned to the high-pressure receiver 122 with the first stage liquid stream in line 110 and second compressed main net gas stream in line 113 downstream of the first compressor 104 and the second compressor 111, so as not to require additional compressor capacity. The rich absorbent stream in line 116 is thus separated into the gaseous hydrocarbon stream in line 123 and the liquid hydrocarbon stream in line 124. A C3+ hydrocarbon rich absorbent stream in line 116 is returned to the second compressed main net gas stream in line 113 prior to chilling. A primary off-gas stream in line 115 from the primary absorber 114 may be directed to a secondary absorber column 118. The primary absorber column 116 may operate a bottoms temperature of about 38° C. to about 62° C. and an overhead pressure of about 1700 kPa to about 2200 kPa.

In the secondary absorber column 118, the primary off-gas stream in line 115 is contacted with a circulating side stream of light cycle oil in line 134 diverted from line 95 taken from the main column 90 which absorbs most of the remaining C5+ and some C3-C4 hydrocarbons in the primary off-gas stream. The secondary absorber column 118 is in downstream communication with the primary absorber column 114. Light cycle oil from the bottom of the secondary absorber column 118 in line 136 rich in C3+ hydrocarbons is returned to the main column 92 via the pump-around for line 95. The overhead of the secondary absorber column 118 transports a dry gas stream comprising predominantly C2-hydrocarbons with hydrogen sulfide, ammonia, carbon oxides and hydrogen in a secondary off-gas stream in line 119. The secondary off-gas stream in line 119 may be processed in a downstream ethylene recovery unit that is not shown. The secondary absorber column 118 may operate a bottoms temperature of about 38° C. to about 60° C. and an overhead pressure of about 1700 kPa to about 2000 kPa.

The liquid hydrocarbon stream in the receiver bottoms line 124 from the high-pressure receiver comprising C3+ hydrocarbons may be transported to a fractionation debutanizer column 140. The fractionation column 140 may be a debutanizer column, a depentanizer column or a dehexanizer column for fractionating the liquid hydrocarbon stream in line 124 into a light hydrocarbon stream in a fractionator overhead line 142 and a heavy hydrocarbon stream in a fractionator bottoms line 144. The fractionation column 140 is ordinarily operated as a debutanizer column but may be operated as a depentanizer column or a dehexanizer column if further cracking is desired for additional olefins production.

The light hydrocarbon stream in fractionation overhead line 142 may be cooled and separated in a fractionation receiver 145 to provide a vapor light hydrocarbon stream in a net fractionation overhead line 117 and a liquid light hydrocarbon in a fractionation receiver bottoms line 146. The fractionation net gas stream in the net fractionation overhead line 117 may be joined with the first compressed main net gas stream in line 106 to be cooled, compressed in the interstage separator 107 and the vapor of which is further compressed in the second compressor 111 to provide the compressed main net gas stream 113. The liquid light hydrocarbon stream in line 146 may be fed to a deethanizer column 150. The heavy hydrocarbon stream in a fractionation bottoms line 144 extending from a bottom of the fractionation column 140 comprising C5+ hydrocarbons from a bottom of the fractionation column 140 is split into the net heavy hydrocarbon stream in the net fractionation bottoms line 148, a reboil stream which is boiled up and returned to the column and a net fractionated product stream in a product line 149. The C5+, C6+ or C7+ hydrocarbons in the net fractionation product line 149 may be further processed as gasoline or petrochemicals. The net heavy hydrocarbon stream in line 148 may be supplemented with the deethanizer overhead liquid stream in a deethanizer receiver bottoms line 156 for supplementing the stripper bottoms stream in line 132 as the primary absorbent in the primary absorbent line 133 to the primary absorber 114. The fractionation column 140 may operate a bottoms temperature of about 190° C. to about 220° C. and an overhead pressure of about 1300 kPa to about 1500 kPa.

The liquid light hydrocarbon stream in the fractionation receiver bottoms line 146 may be deethanized in the deethanizer column 150 to provide a deethanizer overhead stream in line 152 and a deethanized bottom stream in line 154. The deethanizer overhead stream in the deethanizer overhead line 152 may be cooled and separated in a deethanizer receiver 154 to provide a net deethanizer gas stream in a net deethanizer overhead line 155 and the deethanizer overhead liquid stream in the deethanizer receiver bottoms line 156. The net deethanizer gas stream in the net deethanizer overhead line 155 may be added to the gaseous hydrocarbon stream in a high-pressure receiver overhead line 123 to be contacted with the primary absorbent in line 133 including the stripped bottom stream in line 132 to have C3+ hydrocarbons absorbed from the gaseous hydrocarbon stream and the deethanizer gas stream. The deethanizer overhead liquid stream in the deethanizer receiver bottoms line 156 may supplement the net heavy hydrocarbon stream in line 148 which together may supplement the net stripped stream in a net stripper bottoms line 132 as the primary absorbent stream in line 133 to the primary absorbent column 114. The deethanized bottoms stream in the deethanizer bottoms line 154 extending from a bottom of the deethanizer column 140 comprising C3 hydrocarbons from a bottom of the deethanizer column 150 may be split into the net deethanized bottom stream comprising C3 hydrocarbons in a net deethanizer bottoms line 160, and a reboil stream which is boiled up and returned to the column. The net deethanized bottom stream in the deethanizer bottoms line 160 may be taken as a C3 hydrocarbon product stream to a propylene recovery unit which is not shown. The deethanizer column 150 may operate a bottoms temperature of about 36° C. to about 42° C. and an overhead pressure of about 2000 kPa to about 2200 kPa.

EXAMPLE

We simulated operation of the disclosed revamped process and compared it to the conventional process with a stripper downstream of an absorber for a 12,083 m³/day (76,000 bbl/day) unit. The revamp of a conventional unit would likely only require a new refrigeration system at approximately $2M. The disclosed process pushed 20-30% of the reactor vapors to a typically existing gas concentration section generating 20-30% greater margin. We increased the feed rate for an existing FCC unit by about 20% which we estimated would increase gross margin by $69M. The revamped process resulted in no additional operational expense because reduced energy in the gas concentration section due to reduced liquid and vapor loads is balanced against greater low pressure steam use of vapor absorption refrigeration cycle to maintain the propylene recovery in primary absorber.

SPECIFIC EMBODIMENTS

While the following is described in conjunction with specific embodiments, it will be understood that this description is intended to illustrate and not limit the scope of the preceding description and the appended claims.

A first embodiment of the invention is a process for recovering catalytically cracked product comprising contacting a hydrocarbon stream and a stream of catalyst to produce a cracked product stream; fractionating the cracked product stream in a main column; separating an overhead stream from the main column into a main net gas stream and a main overhead liquid stream; and stripping the main overhead liquid stream to provide a stripper overhead stream and a stripped bottom stream. An embodiment of the invention is one, any or all of prior embodiments in this paragraph up through the first embodiment in this paragraph further comprising contacting the stripped bottom stream with a gaseous hydrocarbon stream to absorb C3+ hydrocarbons from a gaseous hydrocarbons stream to provide an absorbed gaseous hydrocarbon stream and a rich absorbent stream. An embodiment of the invention is one, any or all of prior embodiments in this paragraph up through the first embodiment in this paragraph further comprising compressing the main net gas stream to provide a compressed net gas stream and separating the compressed net gas stream to provide the gaseous hydrocarbon stream and a liquid hydrocarbon stream. An embodiment of the invention is one, any or all of prior embodiments in this paragraph up through the first embodiment in this paragraph further comprising fractionating the liquid hydrocarbon stream to provide a light hydrocarbon stream and a heavy hydrocarbon stream. An embodiment of the invention is one, any or all of prior embodiments in this paragraph up through the first embodiment in this paragraph further comprising contacting the gaseous hydrocarbon stream with the heavy hydrocarbon stream to absorb the C3+ hydrocarbons from the gaseous hydrocarbon stream. An embodiment of the invention is one, any or all of prior embodiments in this paragraph up through the first embodiment in this paragraph further comprising separating the rich absorbent stream with the compressed net gas stream to provide the gaseous hydrocarbon stream and the liquid hydrocarbon stream. An embodiment of the invention is one, any or all of prior embodiments in this paragraph up through the first embodiment in this paragraph further comprising separating light hydrocarbon stream into a vapor light hydrocarbon stream and a liquid light hydrocarbon stream and deethanizing the liquid light hydrocarbon stream. An embodiment of the invention is one, any or all of prior embodiments in this paragraph up through the first embodiment in this paragraph further comprising compressing the vapor light hydrocarbon stream with main net gas stream to provide the compressed net gas stream. An embodiment of the invention is one, any or all of prior embodiments in this paragraph up through the first embodiment in this paragraph further comprising contacting the absorbed gaseous stream with a side stream from the main column to further absorb C3+ hydrocarbons from the absorbed gaseous stream to provide a dry gas stream. An embodiment of the invention is one, any or all of prior embodiments in this paragraph up through the first embodiment in this paragraph further comprising recovering ethylene from the dry gas stream.

A second embodiment of the invention is a process for recovering catalytically cracked product comprising contacting a hydrocarbon stream and a stream of catalyst to produce a cracked product stream; fractionating the cracked product stream in a main column; separating an overhead stream from the main column into a main net gas stream and a main overhead liquid stream; stripping the main overhead liquid stream to provide a stripper overhead stream and a stripped bottom stream; and contacting the stripped bottom stream with a gaseous hydrocarbon stream to absorb C3+ hydrocarbons from a gaseous hydrocarbons stream to provide an absorbed gaseous hydrocarbon stream and a rich absorbent stream. An embodiment of the invention is one, any or all of prior embodiments in this paragraph up through the second embodiment in this paragraph further comprising compressing the main net gas stream to provide a compressed net gas stream and separating the compressed net gas stream to provide the gaseous hydrocarbon stream and a liquid hydrocarbon stream. An embodiment of the invention is one, any or all of prior embodiments in this paragraph up through the second embodiment in this paragraph further comprising fractionating the liquid hydrocarbon stream to provide a light hydrocarbon stream and a heavy hydrocarbon stream. An embodiment of the invention is one, any or all of prior embodiments in this paragraph up through the second embodiment in this paragraph further comprising contacting the gaseous hydrocarbon stream with the heavy hydrocarbon stream to absorb the C3+ hydrocarbons from the gaseous hydrocarbon stream. An embodiment of the invention is one, any or all of prior embodiments in this paragraph up through the second embodiment in this paragraph further comprising separating the rich absorbent stream with the compressed net gas stream to provide the gaseous hydrocarbon stream and the liquid hydrocarbon stream. An embodiment of the invention is one, any or all of prior embodiments in this paragraph up through the second embodiment in this paragraph further comprising separating light hydrocarbon stream into a vapor light hydrocarbon stream and a liquid light hydrocarbon stream and deethanizing the liquid light hydrocarbon stream. An embodiment of the invention is one, any or all of prior embodiments in this paragraph up through the second embodiment in this paragraph further comprising compressing the vapor light hydrocarbon stream with main net gas stream to provide the compressed net gas stream. An embodiment of the invention is one, any or all of prior embodiments in this paragraph up through the second embodiment in this paragraph further comprising contacting the absorbed gaseous stream with a side stream from the main column to further absorb C3+ hydrocarbons from the absorbed gaseous stream to provide a dry gas stream. An embodiment of the invention is one, any or all of prior embodiments in this paragraph up through the second embodiment in this paragraph further comprising recovering ethylene from the dry gas stream.

A third embodiment of the invention is a process for recovering catalytically cracked product comprising contacting a hydrocarbon stream and a stream of catalyst to produce a cracked product stream; fractionating the cracked product stream in a main column; separating an overhead stream from the main column into a main net gas stream and a main overhead liquid stream; stripping the main overhead liquid stream to provide a stripper overhead stream and a stripped bottom stream; contacting the stripped bottom stream with a gaseous hydrocarbon stream to absorb C3+ hydrocarbons from a gaseous hydrocarbons stream to provide an absorbed gaseous hydrocarbon stream and a rich absorbent stream; contacting the absorbed gaseous stream with a side stream from the main column to further absorb C3+ hydrocarbons from the absorbed gaseous stream to provide a dry gas stream; and recovering ethylene from the dry gas stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for recovering catalytically cracked product comprising:
   contacting a hydrocarbon stream and a stream of catalyst to produce a cracked product stream;
   fractionating said cracked product stream in a main column;
   separating an overhead stream from the main column into a main net gas stream and a main overhead liquid stream;
   stripping said main overhead liquid stream to provide a stripper overhead stream and a stripped bottom stream; and
   contacting said stripped bottom stream with a gaseous hydrocarbon stream to absorb C3+ hydrocarbons from the gaseous hydrocarbons stream to provide an absorbed gaseous hydrocarbon stream and a rich absorbent stream.

2. The process of claim 1 further comprising compressing said main net gas stream to provide a compressed net gas stream and separating said compressed net gas stream to provide said gaseous hydrocarbon stream and a liquid hydrocarbon stream.

3. The process of claim 2 further comprising fractionating said liquid hydrocarbon stream to provide a light hydrocarbon stream and a heavy hydrocarbon stream.

4. The process of claim 3 further comprising contacting said gaseous hydrocarbon stream with said heavy hydrocarbon stream to absorb said C3+ hydrocarbons from said gaseous hydrocarbon stream.

5. The process of claim 3 further comprising separating light hydrocarbon stream into a vapor light hydrocarbon stream and a liquid light hydrocarbon stream and deethanizing said liquid light hydrocarbon stream.

6. The process of claim 5 further comprising compressing said vapor light hydrocarbon stream with main net gas stream to provide said compressed net gas stream.

7. The process of claim 1 further comprising separating said rich absorbent stream with said compressed net gas stream to provide said gaseous hydrocarbon stream and said liquid hydrocarbon stream.

8. The process of claim 1 further comprising contacting said absorbed gaseous stream with a side stream from said main column to further absorb C3+ hydrocarbons from said absorbed gaseous stream to provide a dry gas stream.

9. The process of claim 8 further comprising recovering ethylene from said dry gas stream.

10. A process for recovering catalytically cracked product comprising:
    contacting a hydrocarbon stream and a stream of catalyst to produce a cracked product stream;
    fractionating said cracked product stream in a main column;
    separating an overhead stream from the main column into a main net gas stream and a main overhead liquid stream;
    stripping said main overhead liquid stream to provide a stripper overhead stream and a stripped bottom stream;
    contacting said stripped bottom stream with a gaseous hydrocarbon stream to absorb C3+ hydrocarbons from the gaseous hydrocarbons stream to provide an absorbed gaseous hydrocarbon stream and a rich absorbent stream;
    contacting said absorbed gaseous stream with a side stream from said main column to further absorb C3+ hydrocarbons from said absorbed gaseous stream to provide a dry gas stream; and
    recovering ethylene from said dry gas stream.

11. A process for recovering catalytically cracked product comprising:
    contacting a hydrocarbon stream and a stream of catalyst to produce a cracked product stream;
    fractionating said cracked product stream in a main column;
    separating an overhead stream from the main column into a main net gas stream and a main overhead liquid stream;
    stripping said main overhead liquid stream to provide a stripper overhead stream and a stripped bottom stream;
    contacting said stripped bottom stream with a gaseous hydrocarbon stream to absorb C3+ hydrocarbons from the gaseous hydrocarbons stream to provide an absorbed gaseous hydrocarbon stream and a rich absorbent stream; and
    compressing said main net gas stream to provide a compressed net gas stream and separating said compressed net gas stream to provide said gaseous hydrocarbon stream and a liquid hydrocarbon stream.

12. The process of claim 11 further comprising fractionating said liquid hydrocarbon stream to provide a light hydrocarbon stream and a heavy hydrocarbon stream.

13. The process of claim 12 further comprising contacting said gaseous hydrocarbon stream with said heavy hydrocarbon stream to absorb said C3+ hydrocarbons from said gaseous hydrocarbon stream.

14. The process of claim 12 further comprising separating light hydrocarbon stream into a vapor light hydrocarbon stream and a liquid light hydrocarbon stream and deethanizing said liquid light hydrocarbon stream.

15. The process of claim 14 further comprising compressing said vapor light hydrocarbon stream with main net gas stream to provide said compressed net gas stream.

16. The process of claim 11 further comprising separating said rich absorbent stream with said compressed net gas stream to provide said gaseous hydrocarbon stream and said liquid hydrocarbon stream.

17. The process of claim 11 further comprising contacting said absorbed gaseous stream with a side stream from said main column to further absorb C3+ hydrocarbons from said absorbed gaseous stream to provide a dry gas stream.

18. The process of claim 17 further comprising recovering ethylene from said dry gas stream.

\* \* \* \* \*